(12) United States Patent
Gudde

(10) Patent No.: US 11,963,805 B2
(45) Date of Patent: Apr. 23, 2024

(54) SHIELDING DEVICE FOR USE IN MEDICAL IMAGING

(71) Applicant: KONINKLIJKE PHILIPS N.V., Eindhoven (NL)

(72) Inventor: Tom Anthony Maarten Gudde, Delft (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 220 days.

(21) Appl. No.: 17/622,314

(22) PCT Filed: Jun. 25, 2020

(86) PCT No.: PCT/EP2020/067791
§ 371 (c)(1),
(2) Date: Dec. 23, 2021

(87) PCT Pub. No.: WO2020/260442
PCT Pub. Date: Dec. 30, 2020

(65) Prior Publication Data
US 2022/0240876 A1    Aug. 4, 2022

(30) Foreign Application Priority Data
Jun. 28, 2019  (EP) .................................... 19183435

(51) Int. Cl.
*A61B 6/10*  (2006.01)
*A61B 6/00*  (2006.01)
*A61B 90/00*  (2016.01)

(52) U.S. Cl.
CPC ............ *A61B 6/107* (2013.01); *A61B 6/4441* (2013.01); *A61B 6/547* (2013.01); *A61B 90/04* (2016.02); *A61B 2090/0436* (2016.02); *A61B 2090/0481* (2016.02)

(58) Field of Classification Search
None
See application file for complete search history.

(56) References Cited

U.S. PATENT DOCUMENTS

| 3,849,649 A | 11/1974 | Carey |
| 4,938,233 A * | 7/1990 | Orrison, Jr. .......... A61B 6/4423 128/853 |
| 2006/0008048 A1 | 1/2006 | Katada |
| 2008/0031422 A1* | 2/2008 | Barkow ................ A61B 6/107 378/203 |

(Continued)

FOREIGN PATENT DOCUMENTS

WO    2014033573 A1    3/2014

OTHER PUBLICATIONS

International Search Report and Written Opinion of PCT/EP2020/067791, dated Oct. 9, 2020.

*Primary Examiner* — Marcus H Taningco

(57) ABSTRACT

An X-ray system is described with a scatter radiation shielding device to be mounted underneath an operating table. The shielding device (10) comprises one or more layers of a radiation blocking material (6) and a cut-out (8) in the one or more layers. The cut-out extends from a point in or near a center of the one or more layers towards an edge to allow radiation transmission to pass. The shielding device is rotatable around a rotation axis. The shielding device substantially reduces the scatter radiation originating from the patient.

15 Claims, 4 Drawing Sheets

(56) References Cited

U.S. PATENT DOCUMENTS

| | | |
|---|---|---|
| 2009/0232282 A1* | 9/2009 | Belson ................. A61B 6/4441 |
| | | 378/209 |
| 2010/0054420 A1 | 3/2010 | Yuan |
| 2012/0132217 A1 | 5/2012 | Rees |
| 2012/0241652 A1 | 9/2012 | Jeschke |
| 2014/0233707 A1 | 8/2014 | Grodzins |
| 2016/0095558 A1* | 4/2016 | Choy ................... A61N 5/1081 |
| | | 600/407 |
| 2016/0220199 A1 | 8/2016 | Gordon |
| 2017/0119324 A1* | 5/2017 | Wilson ..................... G21F 3/00 |
| 2018/0296173 A1 | 10/2018 | Wilson |
| 2019/0336088 A1* | 11/2019 | Gordon .................... G21F 5/02 |

\* cited by examiner

SHIELDING DEVICE FOR USE IN MEDICAL IMAGING

CROSS-REFERENCE TO PRIOR APPLICATIONS

This application is the U.S. National Phase application under 35 U.S.C. § 371 of International Application No. PCT/EP2020/067791, filed on Jun. 25, 2020, which claims the benefit of European Patent Application No. 19183435.7.5, filed on Jun. 28, 2019. These applications are hereby incorporated by reference herein.

FIELD OF THE INVENTION

The present invention is generally related to the field of medical imaging. More is particular, it relates to devices to reduce the direct scatter radiation originating from a patient.

BACKGROUND OF THE INVENTION

During interventional procedures, physicians are guided by imaging techniques such as X-ray imaging. The X-ray source is placed underneath the patient to limit the scatter radiation in the direction of the physicians. Still, the procedure exposes all medical staff in a hybrid operating room environment to a relatively large dose of radiation due to the need for live imaging, therefore resulting in constant x ray exposure during the procedure.

Most of the radiation (e.g., more than 75%) is attenuated in the patient body. One of the largest contributions to this attenuation of radiation, at the photon energy level as used in X-ray imaging (>100 keV or 35 to 60 keV), is Compton scattering. In this form of scattering, the incoming x ray radiation (in the form of a high energy photon) collides with an electron and transfers part of its energy. This excites the electron which can shift to another electron state, while the photon (now with slightly less energy) deflects in a random direction, hence causing the unpredictable nature of scatter radiation.

Compared to the radiation penetrating the patient body, where a great portion of the radiation is attenuated, the scattering underneath the patient and table consists of photons of far greater energy levels which have deflected directly from the patient body. Therefore there is greater hazard for the physicians' health.

To prevent unnecessary health hazards, often lead based shielding is present. Movable ceiling mounted shields are however often misplaced or misused. These shielding solutions need to be repositioned for each change in orientation/position of, for example, a C-arm carrying the radiation source and detector, to protect the physicians properly. The shields can in some instances also hinder the movement of the physicians in the crowded hybrid operating room environment.

Wearable shielding, such as aprons, cause ergonomic discomfort because of the need to be made out of heavy elements (e.g. lead) with a certain thickness (hence, thick and rigid) and are without any pores and gaps (hence, breathable nor flexible).

Consequently, there is a need for improved solutions to reduce or even completely block the scatter radiation from the patient.

SUMMARY OF THE INVENTION

It is an object of embodiments of the present invention to provide for a user-friendly shielding device to lower the scatter radiation from the patient, so that health hazards for physicians are reduced.

The above objective is accomplished by the solution according to the present invention.

In a first aspect the invention relates to a X-ray system having a shielding device comprising one or more layers of a radiation blocking material and a cut-out in the one or more layers. The cut-out extends from a point in or near a center towards an edge of said one or more layers to allow radiation transmission to pass. The shielding device can rotate around a rotation axis.

The proposed solution indeed allows for substantially reducing the scatter radiation. The shielding device allows the radiation to pass via the narrow cut-out in the blocking material. Due to the fact that the device can be rotated around a rotation axis, the cut-out is also rotated, so that any area between the center of the shielding device and the edge can be exposed according to the specific needs.

In certain embodiments, the primary X-ray beam can pass through the shielding device so as to pass through a patient and impinge on an X-ray detector, regardless of the positioning or rotation of the X-ray source. However, due to the radiation blocking material the scatter radiation originating from the patient is substantially reduced. Advantageously, a positioning of the shielding device below a patient table enables a significant reduction in an amount of scattered radiation that is received by physicians or operators in the room.

Thus, in certain embodiments, a shielding solution is proposed to be mounted underneath an operating table to block the direct scatter radiation originating from the patient being treated with a radiation source placed under the operating table. The positioning of the shielding device underneath the operating table is advantageous in that the working area is not intruded, in contrast to ceiling mounted shielding solutions.

The rotation axis is preferably a central axis of the shielding device.

In an advantageous embodiment the shielding device comprises at least one aperture slider to adapt the size of the cut-out. Preferably there are two aperture sliders formed by two sliding plates, each made in said radiation blocking material and arranged to slide at least partially over one another.

In preferred embodiments the shielding device is dome shaped.

In embodiments of the invention actuating means are provided for allowing the shielding device to rotate along its rotation axis.

In certain examples, a frame is provided to mount the shielding device to the bottom side of the patient table. Preferably, the shielding device is mounted in a movable or slideable manner.

Thus, in an example, the shielding device is movably arranged on a ground facing side of the patient table and opposite the X-ray source. In an example, the X-ray system is a C-arm X-ray system, wherein the X-ray source and detector may be rotated about a patient for example with two degrees of freedom of rotational movement.

Advantageously, the shielding device comprises a processor adapted to calculate an intersection point of an X-ray beam emitted by the X-ray source with the patient table based on information on orientation and position of the X-ray source. The processor is further adapted to steer the actuator to position the shielding device in accordance with the calculated intersection point.

In certain examples, a shielding device as described above is movably arranged on a ground facing side of a patient table. That is, the shielding device is arranged on the side of a patient table that faces the X-ray source in a normal orientation of a C-arm system. In this arrangement, X-ray radiation emanating from said X-ray source first passes through the shielding device, prior to being transmitted through a patient on the table and finally impinging on the X-ray detector.

In an example, the shielding device is mounted on a frame fixed underneath the operating table whereon a patient is to be put. The shielding device is then positioned by sliding the shielding device over the frame and/or by rotating the shielding device along the rotation axis. An X-ray source is positioned to allow an X-ray beam to pass via the cut-out of the shielding device and reach the patient at a region of interest. Then the medical imaging can be performed on the patient with the shielding device and the X-ray source in their position.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, wherein like reference numerals refer to like elements in the various figures.

DETAILED DESCRIPTION OF ILLUSTRATIVE EMBODIMENTS

Figure 1:
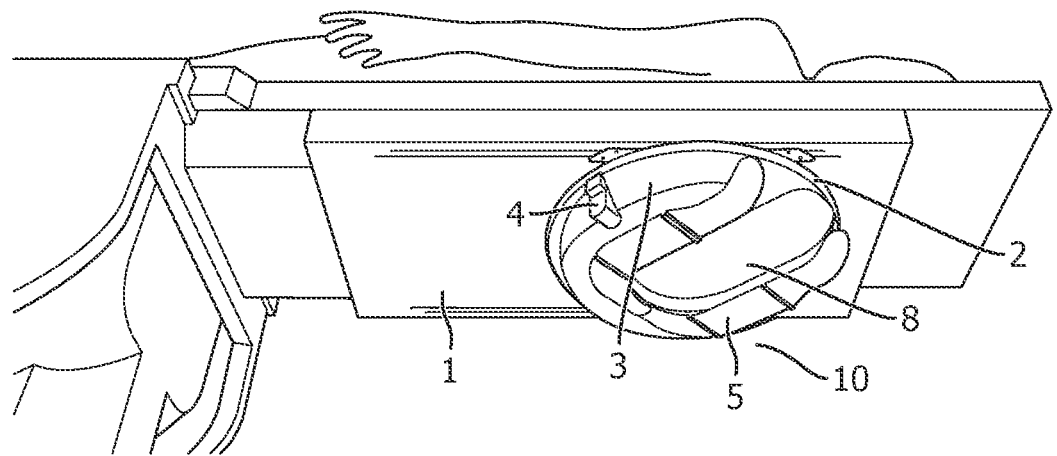
FIG. 1 illustrates an embodiment of the shielding device according to the present invention mounted on a frame underneath an operating table.

An embodiment of a shielding device as used with the present invention is illustrated in FIG. 1. The shielding device (10) has a rotatable structure with one or more plates in a radiation blocking material (6) wherein a narrow cut-out (8) is provided so that radiation transmission can pass. The structure can rotate around a rotation axis, which is in a preferred embodiment the central axis of the shielding device.

The shielding device has in preferred embodiments a dome-like shape, i.e. a dome on a ground surface, and comprises one or more layers (plates) of a radiation blocking material like e.g. lead, tin or aluminium.

The dome-like shielding device features a cut-out in the plating, e.g. lead plating, from a point in or near the center of the plating to the edge of the plating to allow the X-ray beam to enter without being blocked by the lead. In other words, the cut-out is wide enough to let the X-ray beam pass, but narrow enough to have as much surface as possible covered with radiation blocking material in order to reduce the scatter radiation. Due to its ability to rotate around its rotation axis, e.g. its central axis, the dome-like structure allows reaching any point of its ground surface with the X-ray beam. In one embodiment the rotation is performed manually. In a preferred embodiment actuating means (4) are provided to control the rotation. The cut-out therefore also rotates and exposes an area from the center to the edge for a certain rotation. This allows the X-ray beam to pass regardless of the positioning or rotation of the X-ray source itself.

Further, in an X-ray system comprising an X-ray source, a patient table and an embodiment of the shielding device as described herein, the shielding device is movably arranged on a ground facing side of the patient table and opposite the X-ray source, as further detailed below.

Figure 2:
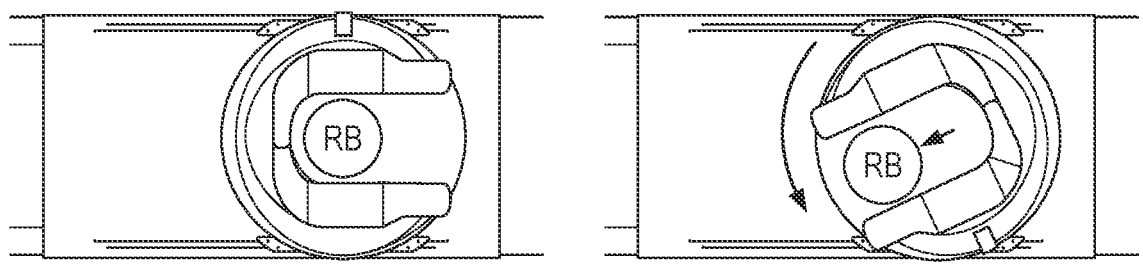
FIG. 2 illustrates two possible positions of the shielding device.
Figure 2:
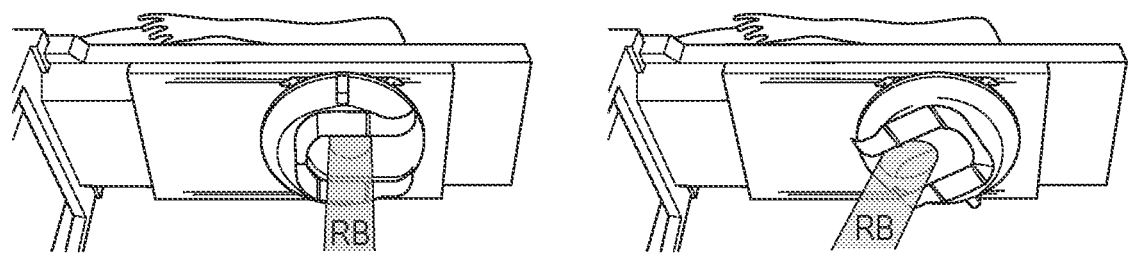

In FIG. 2 two scenarios are illustrated for the relative positioning of the X-ray source and the shielding device. The left hand part of the figure shows a case where the source is placed in a position corresponding to the center of the table. The emitted X-ray beam (RB) is oriented upwards in a vertical direction. In the right hand side example the X-ray source is located at a position away from the center of the table. The incident X-ray beam (RB) now makes an angle different from 90° with respect to the table. Hence, by rotating the cut-out to an appropriate position, the dome-shaped shielding device can allow the X-ray beam (RB) to enter for each movement of the X ray source in both position and orientation.

Scatter radiation originating or reflecting from the patient is then trapped within the radiation blocking elements of the shielding device.

In one embodiment the shielding device comprises an aperture slider that allows narrowing or widening the cut-out with respect to a fixed edge of the cut-out.

Figure 3:
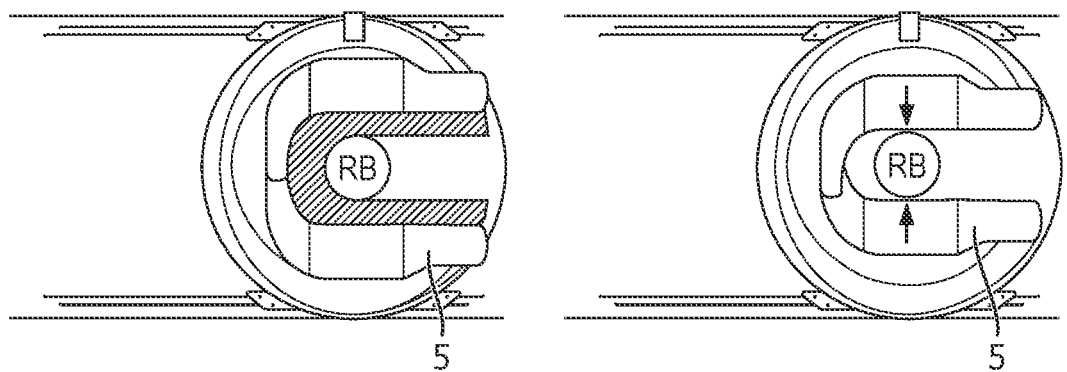
FIG. 3 illustrates two sliding plates of the shielding device, so that the size of the cut-out can be adjusted.

In preferred embodiments there are two aperture sliders. The aperture sliders can advantageously be implemented by means of two sliding plates (5) made of a radiation blocking material, which dilate or contract to widen or narrow the cut-out, as illustrated in FIG. 3. The sliding plates, also referred to as aperture sliders, allow adjusting the size of the cut-out. This feature allows creating a greater shielding surface area by narrowing the cut-out and so reducing unnecessary radiation exposure from scatter that would otherwise pass through the exposed area.

Figure 4:
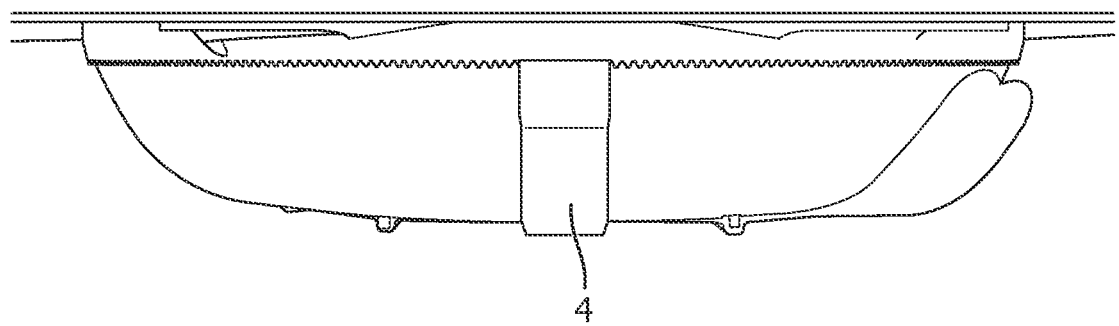
FIG. 4 illustrates a mounting ring provided with gear teeth and an actuator.
Figure 4:
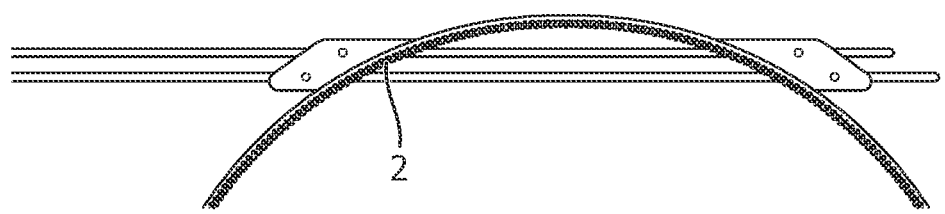

Actuating means (4) for rotating the shielding device can be fixed on the edge of the device. In preferred embodiments a single actuator is employed. The shielding device is in preferred embodiments surrounded by a ring (2) which, besides acting as a fixture for the shielding device, features a set of gear teeth on its edge. In some embodiments the gear teeth are provided over the full 360° of the ring (FIG. 4). In other embodiments there are one or more portions of the ring (which together sum up to less than 360°) that carry gear teeth. The motor-actuator (typically a step motor, although alternative implementations can be considered) pushes on the gear teeth to rotate the shielding device and the position of the cut-out to accommodate for changes in position or orientation of the X-ray source.

Figure 5:
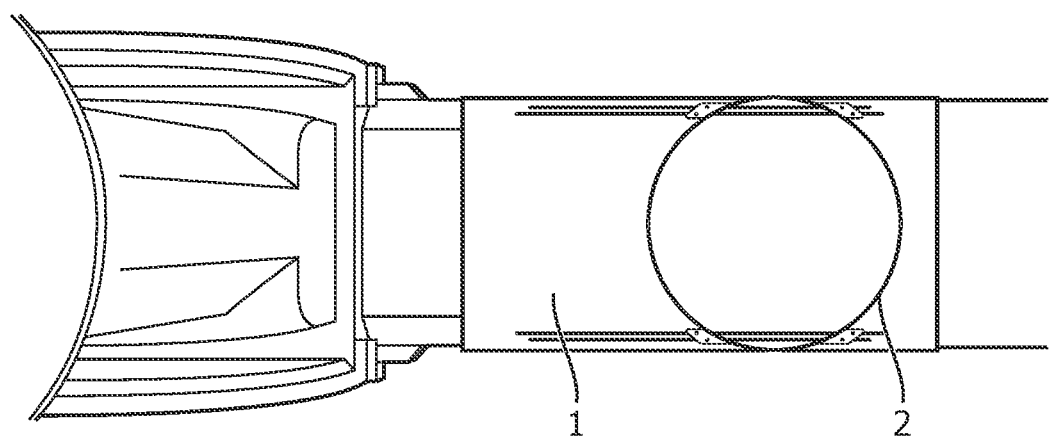
FIG. 5 illustrates a bottom view of the operating table with a frame and a mounting ring.

The shielding device of the present invention can be used as an add-on to existing operating tables in a hybrid operating room. In an advantageous embodiment the shielding device is mounted to a frame (1) attached to the bottom side of the operating table. The present invention also relates to a system comprising a shielding device and a frame. This frame can slide over the operating table and can house the mounting ring with gear teeth for the shielding device as depicted in FIG. 5. This frame and mounting ring are made out of radiolucent material. The central frame can be produced in a variety of widths and heights to allow compatibility with a wide range of operating tables of different dimensions.

Figure 6:
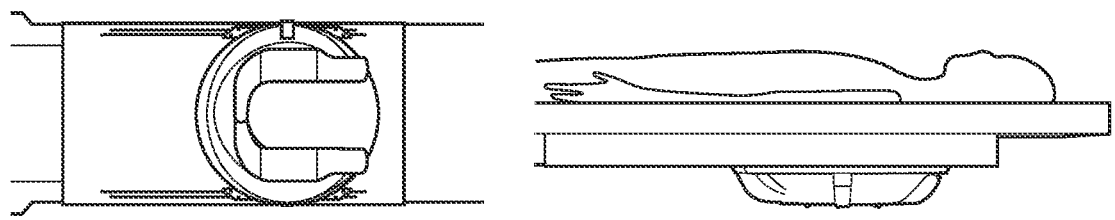
FIG. 6 illustrates a position alteration over the frame.
Figure 6:
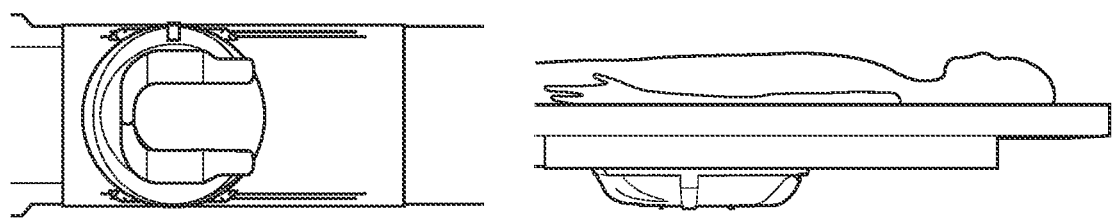

The position of the shielding device and consequently also of the cut-out can be changed by sliding the device over the (bottom side of) the frame to allow for operations in different parts of the body (i.e. in different regions of interest) such as Transcatheter Aortic Valve Implantation (TAVI) or EndoVascular Aneurysm Repair (EVAR) procedures (FIG. 6).

The outer shell (3) of the shielding device is made of lightweight and radiolucent composites. The open shape allows for easy production using various production methods well-known to those skilled in the art (e.g. wet-layup or vacuum infusion).

In some embodiments the composite shell (3) is equipped with several screwhole attachments for an inner layer of the radiation blocking plating. The plates are kept down by gravity and the screws prevent further displacement during operation. This advantageously allows for quick disassembly and repair. An attachment for the motor (4) is positioned on the edge of the composite shell (3).

The plating in a radiation blocking material like e.g. lead is manufactured in the shape of the shielding device, e.g. dome-like shape, and features corresponding holes for the fixtures as mentioned above. As already mentioned the plating may in certain embodiments be a single layer, or, in other embodiments, comprises two or more layers. The plating may have in certain embodiments an equivalent thickness of 0.6 mm. In case lead is used as radiation blocking material such a thickness limits the penetration of the radiation with >95%.

To ensure the system is up to standard with the regulations regarding sterility in an hybrid operating room, the entire shielding device is in preferred embodiments encapsulated (see FIG. 7) within a radiolucent cover (7). This cover can be draped according to regulations and/or hospital protocol. The radiolucent cover may be in radiolucent plastic.

Figure 7:
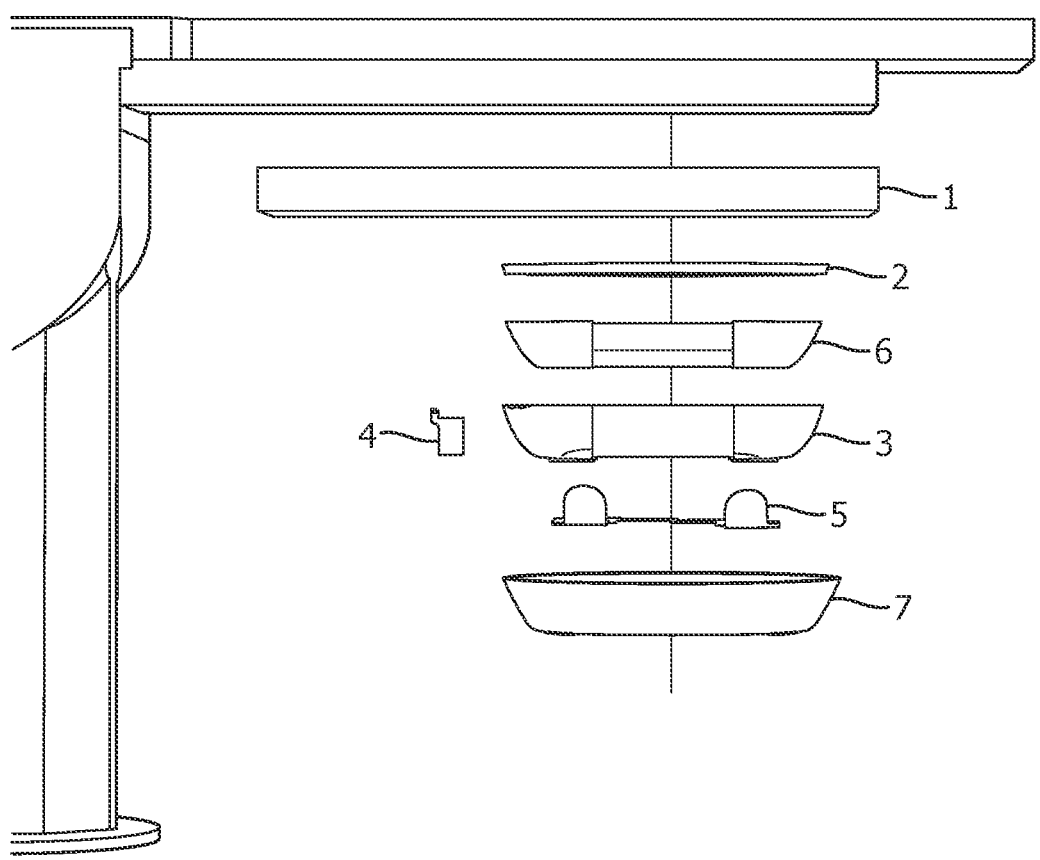
FIG. 7 illustrates various elements of an embodiment of the shielding device according to this invention.

The embodiment shown in FIG. 7 illustrates, from the outer cover (7) moving inwards, the aperture sliders (5), e.g. in a lead composite, the shell (3), e.g. a composite shell, to the shell is connected a motor actuator (4), e.g. a step motor, a radiation blocking lead plating (6), e.g. also in a lead composite, then a table mount, e.g. in radiolucent plastic, and the frame (1), e.g. in a radiolucent plastic, to provide the connection to the operating table.

When an interventional procedure is required in the hybrid operating room, the system is slid in place by a technical staff member. Due to the weight of the plating in a radiation blocking material a dedicated holding mechanism such as a cart may be required during the placement. The shielding device requires data from the X-ray source such as orientation and positioning, therefore it would require a setup to link these components.

Consequently, in advantageous embodiments, the shielding device is arranged for exchanging control data with other devices of the system it is part of. In some of these embodiments the shielding device acts as a slave device, while the device in control of the X-ray source acts as a master. The X-ray source control device conveys to the shielding device the data required for e.g. performing rotation of the shielding device. The shielding device contains a processor, e.g. a microcontroller, which makes calculations based on this data and controls the motion of the actuating means, e.g. the step motor.

In one embodiment the shielding device receives information from the X-ray source on the orientation and position of the X-ray source. Alternatively, a communication hub can be provided at or near the power connection for the shielding device. Communication with the shielding device can then be performed e.g. via wireless communication protocols like WiFi or Bluetooth.

Based on the received data an intersection point of the X-ray beam and the operating table can be calculated. The calculated intersection point is then used to determine the rotation the shielding device should undergo starting from its current position to allow the X-ray beam to penetrate the shielding device and reach the patient and image sensor. The processor then sends a control instruction to the actuating means to carry out the desired rotation, i.e. a rotation with a parameter comprised in the control instruction.

Thanks to the invention the health hazards during cardiac interventions are reduced by lowering the "escaping" scatter radiation at its source, without interfering with the operators or the intervention as a whole.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:
1. An X-ray system comprising:
an X-ray source,
a patient table,. and
a shielding device movably arranged on a ground facing side of the patient table and opposite the X-ray source,
the shielding device comprising one or more layers of a radiation blocking material and a cut-out in the one or more layers, the cut-out extending from a point in or near a center of the one or more layers towards an edge to allow radiation transmission to pass, the shielding device being rotatable around a rotation axis.

2. The X-ray system of claim 1, wherein the rotation axis of the shielding device is a central axis of the shielding device.

3. The X-ray system of claim 1, wherein the shielding device comprises at least one aperture slider for adapting a size of the cut-out.

4. The X-ray system of claim 3, wherein the shielding device comprises two aperture sliders formed by two sliding plates, each made in the radiation blocking material and arranged to slide at least partially over one another.

5. The X-ray system of claim 1, wherein the shielding device is dome shaped.

6. The X-ray system of claim 1, wherein the shielding device comprises an actuator (4) for providing rotation.

7. The X-ray system of claim 6, wherein the actuator is positioned on the edge of the shielding device.

8. The X-ray system of claim 6, comprising a processor arranged for receiving control data to steer the actuator.

9. The X-ray system of claim 1, wherein the shielding device is encapsulated within a radiolucent cover.

10. The X-ray system of claim 1, wherein the shielding device is mounted on a frame fixed underneath the patient table.

11. The X-ray system of claim 10, wherein the frame is made of a radiolucent material.

12. The X-ray system of claim 10, wherein the frame is configured to movably mount the shielding device so that the shielding device is movable along the ground facing side in a longitudinal direction of the patient table.

13. The X-ray system of claim 1, wherein the shielding device comprises a processor configured to calculate an intersection point of an X-ray beam emitted by the X-ray source with the patient table based on information on orientation and position of the X-ray source.

14. The X-ray system of claim 13, wherein the processor is configured to steer the actuator to position the shielding device in accordance with the calculated intersection point.

15. The X-ray system of claim 1, further comprising a C-arm on which the X-ray source and an X-ray detector are mounted.

* * * * *